United States Patent
Harris et al.

(10) Patent No.: US 7,349,094 B2
(45) Date of Patent: Mar. 25, 2008

(54) LASER RADAR APPARATUS HAVING MULTIPLE OUTPUT WAVELENGTHS

(75) Inventors: Michael Harris, Malvern (GB); David J Bryce, Malvern (GB); Guy N Pearson, Malvern (GB); David V Willetts, Malvern (GB)

(73) Assignee: QinetiQ Limited, London (GB)

( * ) Notice: Subject to any disclaimer, the term of this patent is extended or adjusted under 35 U.S.C. 154(b) by 316 days.

(21) Appl. No.: 10/538,042

(22) PCT Filed: Dec. 3, 2003

(86) PCT No.: PCT/GB03/05215

§ 371 (c)(1),
(2), (4) Date: Jun. 8, 2005

(87) PCT Pub. No.: WO2004/053518

PCT Pub. Date: Jun. 24, 2004

(65) Prior Publication Data

US 2006/0114447 A1   Jun. 1, 2006

(30) Foreign Application Priority Data

Dec. 11, 2002  (GB) ................................. 0228890.0

(51) Int. Cl.
   *G01N 21/00* (2006.01)
(52) U.S. Cl. ..................................................... 356/437
(58) Field of Classification Search .................... None
   See application file for complete search history.

(56) References Cited

U.S. PATENT DOCUMENTS

| | | | |
|---|---|---|---|
| 4,410,992 A * | 10/1983 | Javan | 372/32 |
| 5,015,099 A | 5/1991 | Nagai et al. | |
| 5,298,964 A * | 3/1994 | Nelson et al. | 356/33 |
| 5,468,961 A | 11/1995 | Gradon et al. | |
| 5,644,664 A | 7/1997 | Burns et al. | |
| 5,859,611 A | 1/1999 | Lam et al. | |
| 5,973,822 A * | 10/1999 | Xu et al. | 359/308 |
| 7,199,924 B1 * | 4/2007 | Brown et al. | 359/556 |
| 2002/0097874 A1 * | 7/2002 | Foden et al. | 380/256 |

FOREIGN PATENT DOCUMENTS

| | | |
|---|---|---|
| DE | 196 41 515 | 4/1998 |
| JP | 10-10044 | 1/1998 |

OTHER PUBLICATIONS

United Kingdom Search Report for GB 0228890.0 dated Jul. 2, 2003.
International Search Report for PCT/GB03/05215 dated Apr. 8, 2004.
Ridley et al., Improved speckle statistics in coherent differential absorption lidar with in-fiber wavelength multiplexing, *Applied Optics*, vol. 40, No. 12, Apr. 20, 2001, pp. 2017-2023, XP002260851.

* cited by examiner

*Primary Examiner*—Michael P. Stafira
(74) *Attorney, Agent, or Firm*—Nixon & Vanderhye P.C.

(57) ABSTRACT

A coherent laser radar (lidar) device is described. The device has a transmitter portion that comprises a single wavelength laser source, a conversion means (such as an electro-optic modulator) for producing a combined light beam that comprises at least two component light beams of discrete wavelength from the output of said single wavelength laser source, and transmit optics to direct the combined light beam to a remote target. Each component light beam of the combined light beam traverses the same optical path from the single wavelength laser source to the transmit optics. The device is used to make differential absorption measurements.

14 Claims, 3 Drawing Sheets

LASER RADAR APPARATUS HAVING MULTIPLE OUTPUT WAVELENGTHS

This application is the US national phase of international application PCT/GB2003/005215 filed 3 Dec. 2003 which designated the U.S. and claims benefit of GB 0228890.0, filed 11 Dec. 2002, the entire contents of each of which are hereby incorporated by reference.

This invention relates to laser radar (lidar), and in particular to an optical fibre based differential absorption lidar (DIAL) system for real time monitoring and measurement of gaseous species.

A variety of techniques for the measurement of gas concentrations are well known. For example, a number of static sensors are commercially available that allow accurate (parts per billion) localised sampling of a series of gas species. Many of these are "point sensor" devices which draw in a sample and analyse it using classical techniques, such as gas chromatography, flame ionisation or by Fourier Transform Infra-Red (FTIR) spectroscopy. These devices, by their nature, require significant (i.e. greater than is) sampling times and need to be located within the zone of interest.

Alternative techniques are also known which rely on non-dispersive infra-red (NDIR) or non-dispersive ultra-violet (NDUV) absorption. Typically, a series of absorption filters and a broadband source are used to provide light of a wavelength within the narrow absorption bands associated with a gas species of interest. Measurement of the absorption level at the particular wavelength of interest provides a measure of the gaseous concentration, but such systems are typically only capable of capture rates as fast as half a second, and are prone to interfering species.

Differential absorption lidar is another known technique for the remote detection of gas phase constituents. The basic concept of a DIAL system is that two wavelengths of laser light are transmitted by the lidar (light detection and ranging) apparatus. The first wavelength is set at a discrete absorption line of the gas species of interest, whilst the second wavelength is set close to, but away from, the absorption peak. The differential absorption of the first and second wavelengths provides a quantitative measure of the average molecular concentration of the gas species. DIAL techniques thus have an advantage over the alternative techniques described above in that they permit remote detection.

DIAL systems have been implemented in numerous ways; for example analogue, photon-counting and coherent detection systems are known. Coherent detection (or heterodyne) DIAL systems, in which the return radiation is coherently mixed with an optical local oscillator beam, typically provide a high signal to noise ratio with a good degree of immunity to interference from background light and cross-talk. Coherent detection DIAL systems are described in more detail elsewhere; for example see Rye, Appl. Opt. 17, 3862-3864 (1978).

A disadvantage of known coherent DIAL systems is that any fluctuations due to speckle in the return light will lead to a large uncertainty in the detected optical powers unless the received signal is averaged over multiple speckle correlation times. The numerical averaging required to overcome the effects of intensity fluctuations therefore limits the speed at which the differential absorption data can be extracted from the DIAL system.

Recently, a coherent DIAL system has been demonstrated by Ridley et al (see Applied Optics, Vol. 40, No. 12, pp 2017-2023, 20 Apr. 2001) that can reduce the time over which received signals need to be averaged by up to an order of magnitude. The device comprises a pair of laser diodes that are used to produce radiation of two slightly different wavelengths. Local oscillator beams are extracted, and the two different wavelength laser beams are then combined and coupled into a single optical fibre. After combination the two different wavelength beams share a common path through the remaining portion of the transmitter, in free space to/from the target and in the receiver. For small wavelength separations and a shallow target depth, the device exhibits well-correlated speckle fluctuations for the two wavelength channels.

A disadvantage of the system described by Ridley et al is the existence of intensity variations that arise separately in each of the two different wavelength channels prior to beam combination in the transmitter. The presence of such uncorrelated variations increases the time over which the measured intensity signals must be averaged to provide reliable differential absorption data. Alternatively the increased requirement for data averaging can be considered to limit the rate at which differential absorption information having a certain signal to noise ratio can be obtained.

Co-pending PCT patent application GB03/003882 (based on GB application number 0220914.6) describes how the device described by Ridley can be enhanced by providing an additional normalisation signal. However, the improved performance is achieved at the expense of additional device complexity.

It is an object of the present invention to mitigate at least some of the disadvantages described above.

According to a first aspect of the present invention a coherent laser radar (lidar) device has a transmitter portion comprising a single wavelength laser source, a conversion means for producing a combined light beam that comprises at least two component light beams of discrete wavelength from the output of said single wavelength laser source, and transmit optics to direct the combined light beam to a remote target, wherein each component light beam of the combined light beam traverses the same optical path from the single wavelength laser source to the transmit optics.

The present invention thus provides a coherent lidar device in which the two or more component light beams produced for direction to a remote target are provided by the same laser source and travel the same optical path through the transmitter portion. This provides a device in which the majority of noise (e.g. variations of the laser output or noise introduced by the various optical components of the transmitter portion) is common to both the wavelength channels and therefore can be corrected out from the differential absorption information acquired by the device. Furthermore, only a single local oscillator signal is required from the single wavelength laser source to enable coherent detection of any returned signal.

The remote target may comprise a scattering or reflective target that is placed a short distance (e.g. metres) or several kilometers from the device. A skilled person would also recognise that, with an appropriate design of optics, the system could be readily configured to make measurements at much shorter ranges. The scattering or reflective target may be a purpose made scatterer a scatterer of opportunity. Alternatively, the remote target may be an aerosol. A person skilled in the art would recognise the various optical arrangements that would be required to provide a collimated or focussed beam for reflection/scattering from a solid remote target, and how a focussed beam could be obtained to allow measurements from defined target volumes.

It should be noted that the term "light" as used herein includes radiation in the ultraviolet, visible or (near/mid/far) infra-red. As described in more detail below, a person skilled in the art would recognise that a device of the present invention could be implemented across a wide range of wavelengths and in the case of a differential absorption lidar (DIAL) device the precise wavelengths of operation would be selected on the basis of the gas species of interest.

Conveniently, a receiver portion is additionally provided that comprises receive optics to collect light returned from the remote target and a coherent detection means.

Advantageously, each component light beam collected by the receive optics traverses the same optical path from the receive optics to the coherent detection means.

In this case it can be seen that the beams forming the combined beam will be almost totally co-linear; i.e. the beams will follow a common optical path within and outside the device. This minimises instrumental drift that only affects some of the wavelength component beams of the combined beam, thereby reducing the noise associated with any resulting differential absorption data. The device thus gives more robustness against noise sources such as speckle, and provides a reduced rate of false alarms.

Preferably, the conversion means comprises an electro-optic modulator (EOM).

An EOM provides a convenient way of producing the two or more component light beams of discrete wavelength. EOM devices are commercially available; for example, a suitable device is described on page 78 of the 2002/2003 catalogue (Vol. 11) produced by New Focus Inc., 5215 Hellyer Ave, San Jose, Calif. 95138-1001, USA.

Conveniently, the EOM is electrically driven to provide at least three component light beams of discrete wavelength.

Advantageously, the EOM is electrically driven to provide at least five component light beams of discrete wavelength.

The use of three or five or more discrete wavelength channels overcomes the possible opacity effect that can be observed when only two wavelength channels are used. This is described in more detail below with reference to FIG. 4.

Preferably, the transmitter portion additionally comprises a polarisation control means.

The EOM will have an radiation input polarisation at which the amount of power converted in to higher order modes is maximised. A polarisation control means may thus be used to adjust the polarisation of light to maximise EOM conversion efficiency. The device may further or alternatively comprise a polarisation control means configured to control the polarisation state of the received light and/or the extracted component light beam with respect to the polarisation state of the associated local oscillator beam. This allows the heterodyne mixing efficiency at the heterodyne detection means to be controlled (e.g. maximised) by matching the polarisation of the signal and local oscillator beams.

The transmit portion may advantageously further comprise at least one optical amplifier. For example, an erbium doped fibre amplifier (EDFA). The additional of an amplifier enables output signal strength to be increased if the remote target has a low scattering strength (e.g. because it is a distributed target such as an aerosol).

Conveniently, a frequency shifting means is provided to introduce a frequency shift between the laser beam received by the conversion means and its associated local oscillator signal. This enables the contributions to the signal at the different transmitted wavelengths returned from the target to be readily separated.

Preferably at least some of the optical components of the device are interconnected via optical fibre cable. Although the invention is preferably implemented using a fibre optic based device, it should be recognised that some or all of the internal optical components of the device may be optically linked by light beams transmitted through free space. For example, a lens used to transmit the combined beam may receive such light through free space from a fibre end that is located an appropriate distance from the lens.

The width of the detected heterodyne peak may be broadened if the path length (i.e. device to target to device) is significantly greater than the coherence length of the laser. The addition of a delay line to delay the local oscillator beam will reduce this unwanted peak broadening. The local oscillator beam is thus advantageously coupled from the transmitter portion to a receiver portion via an optical fibre delay line.

Preferably, separate transmit optics and receive optics are provided. In other words, the optical components (lenses etc) used to transmit the beam to the remote target are separate to the optical components that are used to collect the returned beam; i.e. the arrangement is bistatic. It should be noted that it is also possible to implement the present invention using common transmit and receive optical components; i.e. a monostatic transceiver configuration.

Advantageously, the wavelength of one of the at least two component light beams is selected to coincide with a peak in absorption of a gas species of interest.

Conveniently, the device further comprises means to vary the wavelength of one or more of the at least two component light beams in response to the detected return signal falling below a threshold level. In other words, if a wavelength channel becomes opaque due to the presence of a high concentration of gas species the transmitted wavelength can be altered so that it falls on a different region of the peak in absorption of the gas species of interest. This increases the dynamic range of the device as described below with reference to FIG. 4.

According to a second aspect of the present invention a lidar device comprises a single laser source and arranged to transmit a beam that comprises three or more wavelength components to a remote target.

Conveniently the device comprises an electro-optic modulator.

The invention will now be described, by way of example only, with reference to the following drawings in which.

Figure 1:
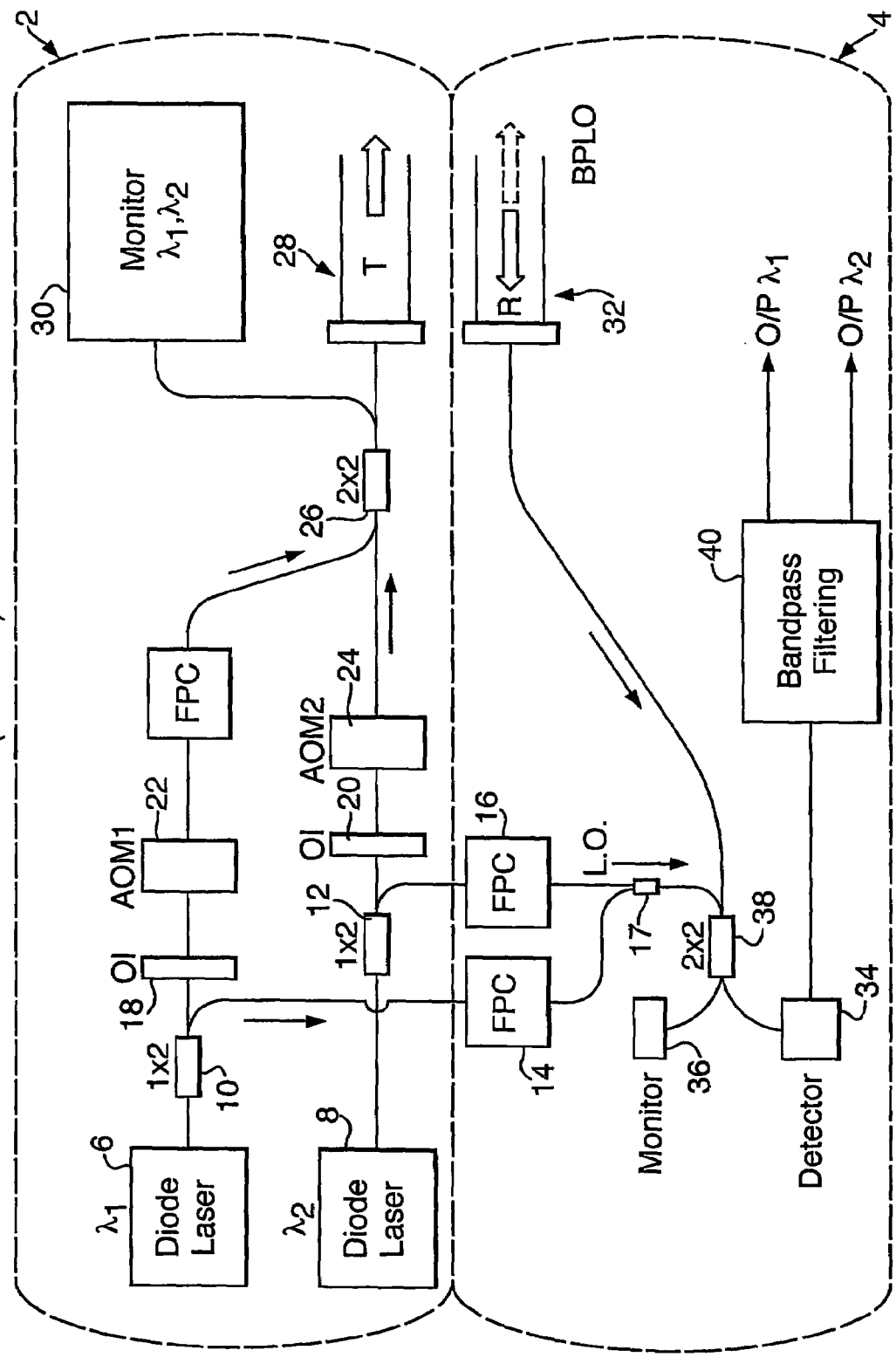
FIG. 1 shows a prior art fibre based DIAL device.

Referring to FIG. 1, prior art coherent DIAL apparatus of the type described by Ridley et al is shown. The apparatus comprises a transmitter portion 2, and a receiver portion 4.

The transmitter portion 2 comprises a first laser 6 and a second laser 8. The first and second lasers are distributed feedback (DFB) semiconductor lasers that operate within a user selectable wavelength range of 1500 nm to 1600 nm and have a linewidth of 20 KHz.

The optical output of the first laser 6 is fed into a first beam-splitter 10 via an optical fibre. The optical output of the second laser 8 is fed into a second beam-splitter 12 via an optical fibre. The first and second beam-splitters 10 and 12 divide each beam they receive into a local oscillator beam and a main beam. The polarisation of each local oscillator beam is adjustable using fibre polarisation controllers 14 and 16 to ensure maximum heterodyne mixing efficiency is obtained in the receive portion.

The two main beams output by the first and second beam-splitters 10 and 12 are fed, via optical isolators 18 and 20, to first and second acousto-optic modulators (AOMs) 22 and 24 respectively. The AOMs 22 and 24 introduce a phase shift between each main beam and its associated local oscillator beam to enable subsequent coherent (heterodyne) detection in the receive portion. A 79 MHz frequency shift is imparted by the first AOM 22, and an 81 MHz frequency shift is imparted by the second AOM 24.

The frequency shifted beams are then combined by beam combiner 26 and coupled into a single optical fibre. The combined beam is transmitted to a remote target via transmission optics 28. A portion of the combined beam is directed, prior to transmission to the remote target, to a laser wavelength monitor 30 to permit the wavelengths of the components of the transmitted beam to be continually measured.

The receiver portion 4 comprises receive optics 32 that collect any radiation returned from the remote target. The return signal is coupled into a single optical fibre cable, mixed with both local oscillator beams that have been combined by beam combiner 17, and fed to a detector 34 and a monitor 36 via a beam combiner/splitter means 38.

Heterodyne mixing at the detector 34 of the return beam and the associated local oscillator beams produces two signals at frequencies corresponding to the difference in frequency of each component of the returned beam and its local oscillator. In this case, a signal at 79 MHz (i.e. the phase shift imparted by the first AOM 22) and a signal at 81 MHz (i.e. the phase shift imparted by the second AOM 24) is detected at the detector 34. The electrical signals produced by the detector 34 are integrated over a narrow bandwidth by a spectrum analyser means 40 that provides electrical output signals indicative of the strength of both of the wavelength components of the returned beam. In this manner, differential absorption data can be obtained.

It can be seen that the two laser sources 6 and 8 produce beams that are of a similar wavelength and, after beam combination in the transmitter portion, the beams pass along the same optical path until detection. Therefore, as described previously by Ridley et al (ibid), any noise due to atmospheric disturbances and/or Pointing instability will be similar for the two different beams and have no significant effect on the measured differential absorption ratio.

Although the two beams pass along the same optical path after combination and prior to detection, there still remains a significant amount of noise introduced prior to beam combination in the beam combiner 26. The noise, for example fluctuations in laser intensity and noise introduced by each AOM, introduces uncertainty into the measured differential absorption data. Although additional normalisation techniques (for example that described in co-pending PCT application GB03/003882) can be employed to improve the quality of the measure differential absorption signal, they tend to involve additional device complexity and/or additional signal processing.

Figure 2:
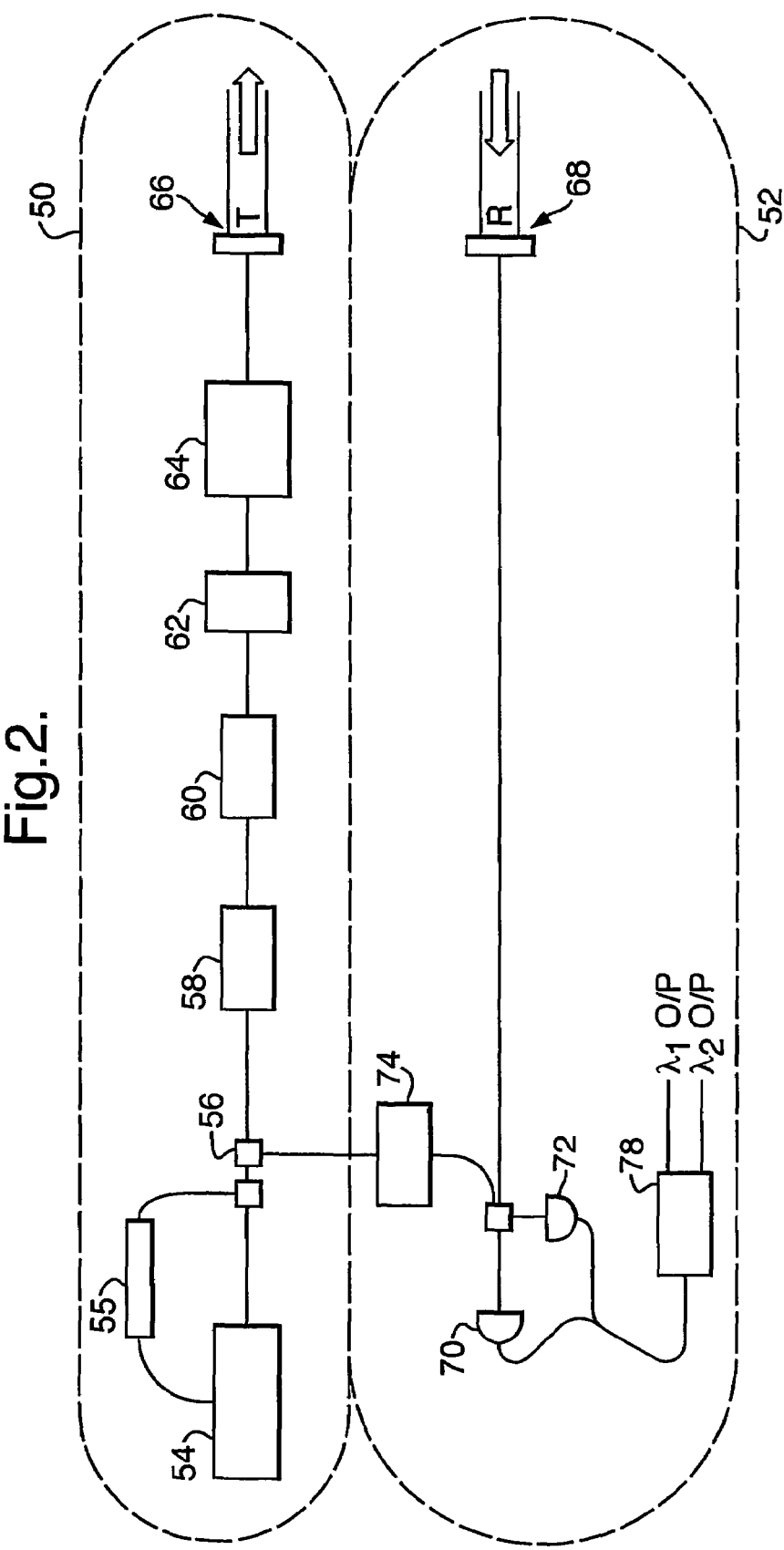
FIG. 2 illustrates an DIAL device according to the present invention.

Referring to FIG. 2, a fibre based DIAL device according to the present invention is shown. The apparatus comprises a transmit portion 50 and a receive portion 52 but, unlike the DIAL device described with reference to FIG. 1, the transmit portion 52 of a device of the present invention comprises only a single laser source 54.

A local oscillator beam is tapped from the output of the laser source using a beam splitter 56 and passed to the receive portion 52 whilst the remaining power of the laser beam is shifted 80 MHz in frequency by an AOM 58. The optical output of the AOM 58 is then fed, via a first polarisation controller 60, to an Erbium doped fibre amplifier (EDPA) 62. The amplified optical signal produced by the EDFA 62 is passed to an electro-optic modulator (EOM) 64. A first polarisation controller 60 is arranged so as to provide a signal having a polarisation that matches the input polarisation required for optimum performance of the EOM 64.

As described in more detail with reference to FIG. 3 below, the EOM 64 converts the single frequency beam it receives into a number of component beams of different frequency. The beam output by the EOM thus comprises a number of collinear beams of different wavelength which form a so-called combined beam (i.e. a beam that is made from the combination of a number of beams of different wavelength) that is transmitted via the transmission optics 66 to a remote target (not shown).

It should be noted that the frequency of light output by the laser 54 in a device of the present invention may be stabilised using a feedback loop. A small proportion of the light output by the laser source 54 could be fed to a feedback means 55. The feedback means 55 is configured to analyse the laser output and to alter the intensity and/or wavelength of the laser source 54 in order to maintain the required laser output.

The receive portion 52 comprises receive optics 68 to collect any radiation returned from the remote target and passes the received beam, via an optical fibre, to a beam combiner/splitter means 70 where it is combined with the local oscillator beam derived from the laser source 54 and fed to a balanced receiver detection system comprising a first receiver 70 and a second receiver 72. The efficiency of the mixing at the detectors is optimised by controlling the polarisation of the local oscillator beam using a second polarisation controller 74.

A balanced receiver detection system of this type has various advantages, albeit with an associated increase in cost and complexity, over the detection system described with reference to FIG. 1. For example, a balanced receiver detection system slightly increases the detected signal strength and reduces the effect of laser intensity noise (RIN). A skilled person would recognise that any appropriate heterodyne detection means could be used in a lidar device of the present invention.

Figure 3:
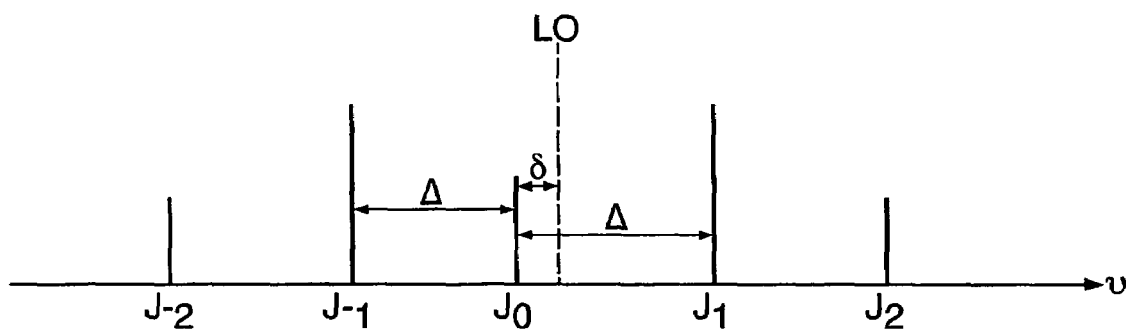
FIG. 3 illustrates the relative intensities and wavelengths of the signals produced by a device of the type shown in FIG. 2 and FIG. 4 demonstrates how a device of the present invention can be used to make differential absorption measurements.

The EOM 62 splits the single wavelength beam produced by the laser into a number of component beams each having a different wavelength as required, and FIG. 3 shows the spectral output of the EOM used in the device described with reference to FIG. 2.

It can be seen from FIG. 3 that the EOM 62 outputs a zeroth order beam $J_0$ at a frequency $\nu-\delta$ where $\nu$ is the frequency of the laser source 54 and $\delta$ is the frequency shift imparted by the AOM 58. First order beams $J_1$ and $J_{-1}$ having an equal intensity are also produced at frequencies $\nu-\delta+\Delta$ and $\nu-\delta-\Delta$ respectively where $\nu$ is the first order frequency shift imparted by the EOM and would typically be around 500 MHz. Second order beams $J_2$ and $J_{-2}$, of a different frequency and of a lower intensity than the first order beams, are also output.

As the local oscillator beam has a frequency $\nu$ (i.e. it is tapped from the transmission portion prior to application of a frequency shift by the AOM 58), each of the signals $J_0$, $J_{-1}$, $J_{+1}$, $J_{-2}$, $J_{+2}$ etc will produce a corresponding heterodyne signal at the detectors 70 and 72 of a unique frequency. A spectrum analyser 78 is used to integrate the electrical signals produced by the detectors 70 and 72 over a narrow bandwidth in order to provide electrical output signals indicative of the strength of each of the signals $J_0$, $J_{-1}$, $J_{+1}$, $J_{-2}$, $J_{+2}$ etc. In this manner, differential absorption data can be obtained. Any systematic distortion of the differential absorption ratio (e.g. systematic errors arising due to non-uniform frequency response of the detectors) can be removed using standard calibration techniques. Although a spectrum analyser 78 is shown, it would be recognised that band pass filters combined with an electrical power meter could be used as an alternative.

It should be noted that the electrical power applied to the EOM 62 defines the proportion of optical power that is frequency shifted to the higher order beams from the zeroth order beam, whilst the frequency of the RF signal applied to the EOM defines the magnitude of the frequency shift $\Delta$. The use of an EOM thus provides a means of controlling the wavelengths of the component beams that are generated in the transmission portion of the device.

As described above, the EOM 62 operates most efficiently when it receives light of a certain polarisation and hence the use of the first polarisation controller 60. However, it should be noted that inputting a non-optimum polarisation to the EOM only reduces the efficiency with which it frequency shifts radiation into the higher order beam; i.e. the ratio of the optical power in, say, each of the first order beams remains constant.

Figure 4:
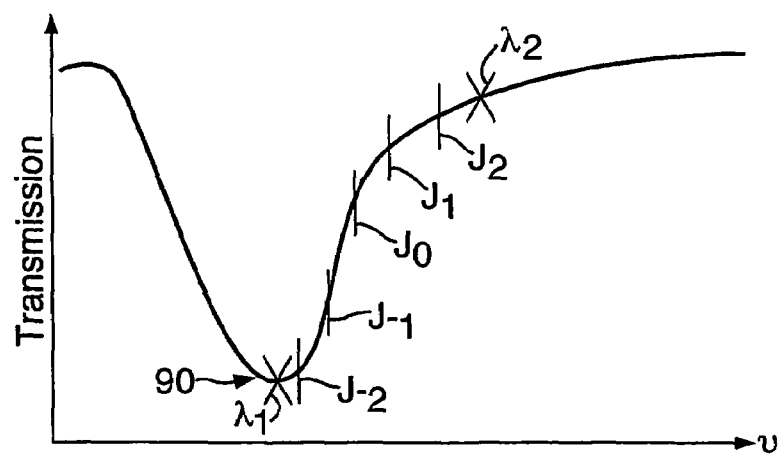

Referring to FIG. 4, additional advantages of using a device of the present invention are shown.

In conventional DIAL lidar devices, two beams of slightly different wavelength (e.g. $\lambda_1$ and $\lambda_2$) are used. One wavelength (e.g. $\lambda_1$) is chosen to coincide with an absorption peak (e.g. the transmission trough 90) and the other wavelength (e.g. $\lambda_2$) is selected to be away from, or at the edge of, that peak. The relative difference in absorption of wavelength $\lambda_1$ compared to $\lambda_2$ provides an indication of the concentration of the gaseous species of interest. However, if a large amount of the gas species is present virtually all of the radiation at wavelength $\lambda_1$ will be absorbed by the gas. This "bottoming out" or opacity of the $\lambda_1$ channel effectively places an upper limit on the concentration of the gas that can be accurately measured; i.e. it reduces the dynamic range of the device.

A device of the present invention permits the opacity effect observed with dual wavelength lidar systems to be overcome by simultaneously measuring the absorption at a number (e.g. five) of discrete wavelengths. For example, taking the system described with reference to FIGS. 2 and 3, the five beams of different wavelength ($J_0$, $J_{-1}$, $J_{+1}$, $J_{-2}$, $J_{+2}$) output by the device can be spread across the absorption peak of the gas species of interest as shown in FIG. 4. In this case, if the signal returned from beam $J_{-2}$ becomes opaque, the absorption of the other beams near the absorption peak (e.g. beams $J_{-1}$, $J_0$ and $J_{+1}$) can still be measured relative to the $J_{+2}$ beam.

In an alternative configuration the device could be arranged to normally output three beams of different wavelength (e.g. $J_0$ and $J_{\pm 1}$), but could also comprise a means of increasing the power applied to the EOM to provide higher order beams (e.g. $J_{\pm 2}$) if any of the three initial signals become opaque. A device of the present invention can thus be seen to have a greater dynamic range, and to be generally more flexible, than dual wavelength DIAL systems.

A person skilled in the art would recognise the various alternative optical arrangements that could used to implement the present invention. For example, the various optical components making up the transmission portion could be altered in order and still provide a system that provides substantially the same function. The feedback mechanism used to stabilise the output of the laser source could also be changed so as to use light tapped out of the main optical path at any of a variety of point, such as after the EOM.

The apparatus could also be configured to measure the differential absorption properties of a gaseous species that is moving relative to the DIAL device. For example, the apparatus could be operated from a moving aircraft or vehicle. In such a case, a skilled person would recognise the Doppler shift effects due to the relative motion that would also need to be considered to ensure proper operation of the DIAL device.

Although bistatic transceivers (i.e. transceivers having separate transmit and receive optics) are described above, a person skilled in the art would recognise that monostatic transceivers (i.e. transceivers having combined transmit and receive optics) could be used. Monostatic device would be particularly useful when using a pulsed transmit beam. Similarly, it would be recognised by a skilled person that although optical fibre based systems are preferred for many reasons (e.g. ease of component alignment, cost etc) the present invention could also be implemented using free space optical components.

The device described above employs a laser that emits radiation in the 1500 nm to 1600 nm range. However, the invention could be implemented using radiation of any wavelength. A skilled person would recognise that the wavelength of the laser source would simply be selected so that the output radiation matches the absorption maxima of the gas species of interest. As laser diode technology develops, it will thus become possible to cheaply access wavelengths further into the infrared using this technique. The use of an increased wavelength may be a considerable advantage for differential absorption measurements of species such as carbon monoxide, nitrogen oxides and unburned hydocarbons.

The invention claimed is:

1. A coherent laser radar (lidar) device having a transmitter portion that comprises a single wavelength laser source, a converter for producing a combined light beam that comprises at least two component light beams of discrete wavelength from the output of said single wavelength laser source, and transmit optics to direct the combined light beam to a remote target, wherein each component light beam of the combined light beam traverses the same optical path from the single wavelength laser source to the transmit optics.

2. A device according to claim 1 wherein a receiver portion is additionally provided that comprises receive optics to collect light returned from the remote target and a coherent detector.

3. A device according to claim 2 wherein each component light beam collected by the receive optics traverses the same optical path from the receive optics to the coherent detector.

4. A device according to claim 1 wherein the converter comprises an electro-optic modulator (EOM).

5. A device according to claim 4 wherein the EOM is electrically driven to provide at least three component light beams of discrete wavelength.

6. A device according to claim 4 wherein the EOM is electrically driven to provide at least five component light beams of discrete wavelength.

7. A device according to claim 4 wherein the transmitter portion additionally comprises a polarisation controller.

8. A device according to claim 1 wherein the transmit portion further comprises at least one optical amplifier.

9. A device according to claim 1 wherein a frequency shifter is provided to introduce a frequency shift between the laser beam received by the converter and its associated local oscillator signal.

10. A device according to claim 1 wherein at least some of the optical components of the device are interconnected via optical fibre cable.

11. A device according to claim 10 wherein the local oscillator beam is coupled from the transmitter portion to a receiver portion via an optical fibre delay line.

12. A device according to claim 1 wherein separate transmit optics and receive optics are provided.

13. A device according to claim 1 wherein the wavelength of one of the at least two component light beams is selected to coincide with a peak in absorption of a gas species of interest.

14. A device according to claim 13 wherein the wavelength of at least one of said at least two component light beams is varied when the detected return signal falls below a threshold level.

* * * * *